US012447289B2

(12) United States Patent
Stuart

(10) Patent No.: US 12,447,289 B2
(45) Date of Patent: Oct. 21, 2025

(54) PORTABLE INHALER

(71) Applicant: MERXIN LTD, King's Lynn (GB)

(72) Inventor: Adam Stuart, King's Lynn (GB)

(73) Assignee: Merxin Ltd., King's Lynn (GB)

( * ) Notice: Subject to any disclaimer, the term of this patent is extended or adjusted under 35 U.S.C. 154(b) by 586 days.

(21) Appl. No.: 17/620,913

(22) PCT Filed: May 26, 2020

(86) PCT No.: PCT/IB2020/054958
§ 371 (c)(1),
(2) Date: Dec. 20, 2021

(87) PCT Pub. No.: WO2021/001704
PCT Pub. Date: Jan. 7, 2021

(65) Prior Publication Data

US 2022/0323696 A1 Oct. 13, 2022

(30) Foreign Application Priority Data

Jul. 1, 2019 (GB) ..................................... 1909482

(51) Int. Cl.
*A61M 11/00* (2006.01)
*A61M 11/08* (2006.01)
*A61M 15/00* (2006.01)

(52) U.S. Cl.
CPC ......... *A61M 11/006* (2014.02); *A61M 11/007* (2014.02); *A61M 15/00* (2013.01); (Continued)

(58) Field of Classification Search
CPC .. A61M 11/007; A61M 11/006; A61M 15/00; A61M 11/08; A61M 15/0001; A61M 11/00; A61M 15/0065; A61M 2205/58
See application file for complete search history.

(56) References Cited

U.S. PATENT DOCUMENTS 5,394,866 A 3/1995 Ritson et al.
6,321,952 B1 11/2001 Cassier et al.
(Continued)

FOREIGN PATENT DOCUMENTS

CN 1203533 A 12/1998
CN 103038141 A 4/2013
(Continued)

OTHER PUBLICATIONS

Search Report under Section 17 issued in GB Patent Application No. GB1909482.0, on Dec. 13, 2019, 3 pages.
(Continued)

*Primary Examiner* — Tu A Vo
(74) *Attorney, Agent, or Firm* — Andrus Intellectual Property Law, LLP

(57) ABSTRACT

A portable inhaler, has a rotary actuation mechanism, including a follower component (104), a rotary loading device (106) and a button (112). The rotary loading device has a cam component (108) engaged with a cage component (110), to allow a predetermined limited rotational relative movement therebetween. The button is translatable between a central position and an extended position, and can be engaged by the cam component upon rotary movement of the rotary actuation mechanism to its primed position to translate the button to its extended position, and the button can engage the cam component to effect rotary movement of the rotary actuation mechanism to its actuated position as the button translates to its central position thereby releasing the follower component.

19 Claims, 12 Drawing Sheets

(52) U.S. Cl.
CPC .... *A61M 15/0001* (2014.02); *A61M 15/0065* (2013.01); *A61M 11/08* (2013.01)

(56) References Cited

U.S. PATENT DOCUMENTS

| | | | | |
|---|---|---|---|---|
| 2003/0042336 | A1* | 3/2003 | Wuttke | A61M 15/0065 239/569 |
| 2004/0025870 | A1* | 2/2004 | Harrison | B29C 45/14336 128/202.17 |
| 2009/0020114 | A1* | 1/2009 | Brambilla | A61P 11/00 128/200.23 |
| 2012/0216805 | A1 | 8/2012 | Brunnberg et al. | |
| 2015/0020798 | A1* | 1/2015 | Elgaard | A61M 15/0025 128/200.23 |
| 2015/0174346 | A1 | 6/2015 | Dhuppad et al. | |
| 2015/0320947 | A1* | 11/2015 | Eicher | A61M 11/00 128/200.14 |
| 2015/0359978 | A1* | 12/2015 | Egerström | A61M 5/31515 128/200.14 |
| 2016/0206559 | A1 | 7/2016 | Dalvi et al. | |
| 2017/0128680 | A1 | 5/2017 | Eicher et al. | |
| 2019/0022339 | A1* | 1/2019 | Richardson | A61M 15/009 |
| 2021/0008302 | A1* | 1/2021 | Treneman | A61M 15/0013 |
| 2022/0054775 | A1* | 2/2022 | Säll | A61M 15/0073 |

FOREIGN PATENT DOCUMENTS

| | | | |
|---|---|---|---|
| CN | 103582505 | A | 2/2014 |
| CN | 108348701 | A | 7/2018 |
| CN | 109689136 | A | 4/2019 |
| FR | 2774312 | A1 | 8/1999 |
| GB | 2291135 | A | 1/1996 |
| JP | 2000501957 | A | 2/2000 |
| JP | 2013523317 | A | 1/2017 |
| JP | 2017148556 | A | 8/2017 |
| WO | 9712687 | A1 | 4/1997 |
| WO | 9720590 | A1 | 6/1997 |
| WO | 0170315 | A1 | 9/2001 |
| WO | 2018048786 | A1 | 3/2018 |
| WO | 2020064372 | A1 | 4/2020 |

OTHER PUBLICATIONS

International Search Report and Written Opinion of the International Searching Authority issued in International Patent Application No. PCT/IB2020/054958 on Sep. 23, 2020, 10 pages.

Notification concerning Transmittal of International Preliminary Report on Patentability mailed in International Patent Application No. PCT/IB2020/054958 on Jan. 13, 2022, 7 pages.

Communication of a Notice of Opposition in corresponding European Application No. 20743241.0, dated Jan. 5, 2024, 26 pages.

Decision Rejecting the Opposition in corresponding European Application No. 20743241.0, dated Apr. 9, 2025, 34 pages.

Certified Priority Document of European Application No. 19162982.3, filed Mar. 14, 2019, made available on Apr. 2, 2020, in International Application PCT/EP2019/074569.

* cited by examiner

PORTABLE INHALER

TECHNICAL FIELD

The present disclosure relates generally to medical devices, and particularly to drug inhalers; and more specifically, to loading and actuation mechanism for a drug inhaler.

BACKGROUND

Drug inhalers have long been utilised for delivering medication for treating diseases related to lungs, respiration, and the like. The drug inhalers are capable of dispensing small quantities of fluids (such as pharmaceutical compounds, drugs, and the like) within flow rates of micro/millilitres per minute. The manufacturing of such drug inhalers is of special interest as a robust fluid delivery method in a host of important applications such as controlled and accurate drug delivery. Typically, the drug inhalers that are taken in practise, functions in a way that a metered amount of drug dose is loaded and triggered through a narrow outlet (such as, nozzle).

Most inhaler devices are designed to be loaded prior to use and then actuated using a simple, low force button press. This low force operation makes using the device much easier and can improve coordinating the dose with the inhalation. This is of particular importance in a soft mist inhaler as the force required to deliver a dose is often very high (typically >40N). For such purpose, the employed mechanism would need to be easily loaded by the patient but also need to remain robust and stable in its loaded state prior to actuation. The force to actuate the device should be low enough, that actuating the device does not impact the drug delivery and the location of the button should be comfortable and readily accessible by the patients. In case of soft mist inhaler, the mechanism needs to hold back a large force (~45N) and have a light trigger force, ideally 5-15 N.

Some existing propellant-free drug inhaler devices deliver medication in the form of mist using the energy released from a tensioned spring. For instance, such device may use a cam surface which is driven to a point at which it falls off the cliff to a tensioning position. At this tensioning position, the employed mechanism is prevented from further travel by the actuation button obstructing is travel. Once the button is pressed (in a direction perpendicular to the firing axis, the mechanism continues to fires the device. The force required to actuate the button is directly related to the force of the spring and the friction between the button ring and the mechanism cam.

However, one downside of this approach is that some liquid can get expelled from the nozzle and pools at the nozzle exit. This pooling can have an effect on the performance of the actuation which follows the tensioning step. A small amount of liquid at the nozzle can cause an irregular droplet size profile and in some cases drag the spray plume off to one side. Such improper functioning of drug inhalers could possibly lead to inaccurate drug delivery, high risk of failure of device, and the like.

Therefore, in light of the foregoing discussion, there exists a need to overcome the aforementioned drawbacks associated with functioning and design of drug inhalers.

SUMMARY

The present disclosure seeks to provide a portable inhaler. The present disclosure, specifically, seeks to provide a loading and actuating mechanism for the portable inhaler.

The present disclosure seeks to provide a solution to the existing problem of robustness of the inhalers while loading and dispensing of dosages. An aim of the present disclosure is to provide a solution that overcomes at least partially the problems encountered in prior art, and provides robust portable inhaler having a secure loading and actuating mechanism.

In one aspect, an embodiment of the present disclosure provides a portable inhaler, having a rotary actuation mechanism moveable sequentially and alternately between primed positions and actuated positions and comprising;

- a follower component, which is releasable to dispense a dose as the rotary actuation mechanism moves from the primed position to the next actuated position, and able to be primed as the rotary actuation mechanism moves from the actuated position to the next primed position;
- a rotary loading device, the rotary loading device comprising a cam component and a cage component wherein the cam component is caged by the cage component and engaged therewith by mutually interfering mechanical features such as to allow a predetermined limited rotational relative movement between the cage component and the cam component;
- a button, which is translatable between a central position and an extended position, and which can be engaged by the cam component upon rotary movement of the rotary actuation mechanism to its primed position to translate the button to its extended position, and which can engage the cam component to effect rotary movement of the rotary actuation mechanism to its actuated position as the button translates to its central position thereby releasing the follower component.

Optionally, the cam component has a cam tooth which is a radial tooth, the radial tooth having a first cam tooth surface on a leading edge of the tooth and a second cam tooth surface on a trailing edge of the tooth.

Further optionally, the button comprises a diversionary tooth having a first tooth surface engageable by the first cam tooth surface of the radial cam of the cam component upon rotary movement of the rotary actuation mechanism to its primed position to translate the button to its extended position, the diversionary tooth having a second tooth surface which can engage the second cam tooth surface of the radial cam to effect rotary movement of the rotary actuation mechanism to its actuated position as the button translates to its central position thereby releasing the follower component.

Embodiments of the present disclosure substantially eliminate or at least partially address the aforementioned problems in the prior art, and enables a secure loading and actuating mechanism for accurate and precise delivery of medication through drug inhalers.

Optionally, the portable inhaler has a longitudinal axis, wherein the follower component is releasable in a dispensing longitudinal direction and able to be primed in a metering longitudinal direction, and rotary movement of the rotary actuation mechanism is about the longitudinal axis.

Optionally, movement of the follower component is fixed with respect to rotary movement of the rotary actuation mechanism.

Optionally, the button is translatable transverse to the longitudinal axis.

Optionally, the predetermined limited relative rotational movement is in the range 2 to 30 degrees.

Optionally, the rotary movement of the rotary loading device between successive actuated positions of the rotary actuation mechanism is 180 degrees.

Optionally, the cage component has an inward facing recess into which an outward facing projection of the cam component fits loosely to provide the mutually interfering mechanical features.

Optionally, the cage component has an upward facing recess into which the diversionary tooth of the button fits loosely to allow the diversionary tooth to move into the upward facing recess, while the recess rotates about the longitudinal axis.

Optionally, the rotary loading device and the follower component have a mutual helical camming arrangement, such that at least one of the rotary loading device and the follower component has a helical cam configured to engage an opposed camming feature of the opposite component to effect translation of the follower component in a metering longitudinal direction by relative rotation of the rotary loading device and the follower component.

Optionally, the cam component and the follower component have the mutual helical camming arrangement.

Optionally, the cam component has a helical cam.

Optionally, the opposed camming feature is a zero-pitch ledge extending radially from the follower component.

Optionally, the cam component has a zero-pitch extension to the helical cam and the follower component has a zero-pitch opposed camming feature to block movement of the follower in a dispensing longitudinal direction, and an edge to the zero-pitch extension beyond which movement of the follower in its dispensing longitudinal direction is allowed.

Optionally, the follower component is biased in the dispensing longitudinal direction by a spring.

Optionally, the rotary actuation mechanism is moved from its actuated position to its primed position by applying a torque to the cage component.

Optionally, the portable inhaler is a low volatility liquid atomizer.

Optionally, the energy of atomization is provided by a stored mechanical force.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1A:
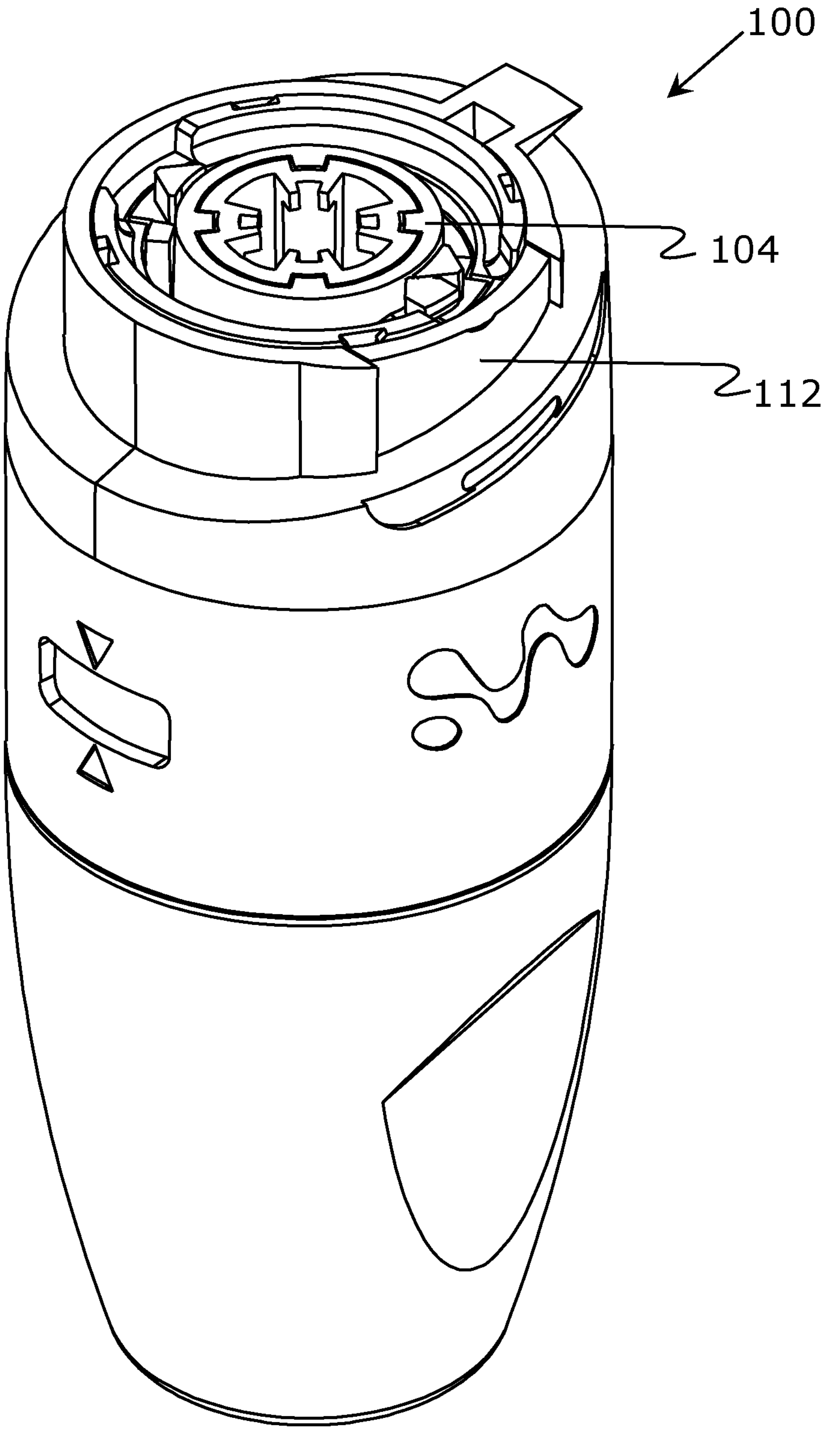
FIG. 1A is a perspective view of a portable inhaler, in accordance with an embodiment of the present disclosure, sectioned horizontally to reveal a top portion of the rotary actuation mechanism.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a portable inhaler, having a rotary actuation mechanism moveable sequentially and alternately between primed positions and actuated positions and comprising;

- a follower component, which is releasable to dispense a dose as the rotary actuation mechanism moves from the primed position to the next actuated position, and able to be primed as the rotary actuation mechanism moves from the actuated position to the next primed position;
- a rotary loading device, the rotary loading device comprising a cam component and a cage component wherein the cam component is caged by the cage component and engaged therewith by mutually interfering mechanical features such as to allow a predetermined limited rotational relative movement between the cage component and the cam component;
- a button, which is translatable between a central position and an extended position, and which can be engaged by the cam component upon rotary movement of the rotary actuation mechanism to its primed position to translate the button to its extended position, and which can engage the cam component to effect rotary movement of the rotary actuation mechanism to its actuated position as the button translates to its central position thereby releasing the follower component.

Optionally, the cam component has a cam tooth which is a radial tooth, the radial tooth having a first cam tooth surface on a leading edge of the tooth and a second cam tooth surface on a trailing edge of the tooth.

Further optionally, the button comprises a diversionary tooth having a first tooth surface engageable by the first cam tooth surface of the radial cam of the cam component upon rotary movement of the rotary actuation mechanism to its primed position to translate the button to its extended position, the diversionary tooth having a second tooth surface which can engage the second cam tooth surface of the radial cam to effect rotary movement of the rotary actuation mechanism to its actuated position as the button translates to its central position thereby releasing the follower component.

The present disclosure provides a portable inhaler having a loading and actuating mechanism. Embodiments of the present disclosure provides a robust inhaler for precise and accurate drug dispensing. Furthermore, the actuating mechanism enables a very low triggering force for actuation, in the range of 5N to 15N. Notably, the actuating mechanism dispenses the drug at a force more than 40N. Beneficially, a low triggering force makes the portable inhaler user friendly and enables better coordination for usage of the portable inhaler.

Throughout the present disclosure, the term "portable inhaler" relates to aerosol drug dose dispensers, that delivers a predetermined amount of medication in a form of spray, which is inhaled by a user (such as a patient). Furthermore, portable inhalers are referred to micro liquid dispensing systems employed to dispense a fluid in small quantities with increased accuracy. The portable inhalers can control and manipulate small volumes of fluid (generally in micrometric volumes). Typically, a pressure force is exerted to dispense the fluid from the portable inhaler through a narrow outlet (such as a nozzle). Furthermore, the narrow outlet allows the fluid to be delivered with a higher pressure. Moreover, the portable inhalers mimic a shape of a cylinder, and has a length that could easily be held in a palm of the user. The portable inhaler includes a container (which contains the fluid) that is detachably attached inside the inhaler, and may be detached when not in use. Notably, a metered dose is drawn from the container, and delivered through the nozzle.

The metered dose may be dispensed using a micropump. The micropump typically comprises a pump body, including a metering chamber, a capillary for delivering a fluid to the metering chamber and a piston for expelling the metered liquid. Materials used for manufacturing the components of the micropump include, but are not limited to, metals, alloys, non-metals (such as semi hardened polyvinyl materials, polymeric materials, glass) or a combination thereof. In an embodiment, at least one of the components of the micropump, i.e. the body, including the metering chamber, the capillary and the piston, is manufactured using polyoxymethylene, commonly referred to as Acetal.

Throughout the present disclosure, the term "fluid" refers to a substance that undergoes a deformation in shape and/or volume when subjected to an external force. The fluid is typically a liquid and/or a dose (drug dosage). It will be appreciated that such substances are required to be delivered by the portable inhaler in small quantities for delivery of accurate volume and at precise locations of delivery. Examples of the fluid include, but are not limited to, inhalation aerosol drug formulations, pharmaceutical compounds, and the like. One aspect of inhalation drug formulations is the need to provide a spray with a droplet size small enough to penetrate to the lungs. In order to produce such a spray by forcing fluid through nozzles, it is necessary to force the fluid at high pressure, e.g. 10 to 59 MPa.

The portable inhaler has the rotary actuation mechanism moveable sequentially and alternately between primed positions and actuated positions. The term "rotary actuation mechanism" used herein relates to an arrangement of mechanical components to provide a drug stroke on actuation thereof. In an example, the mechanical components may include cylindrical elements, circular elements, and the like. The rotary actuation mechanism attains two states that are primed positions and actuated positions. The primed positions and the actuated positions are rotational positions, when the rotary actuation mechanism is rotated clockwise or counterclockwise. Notably, both the primed positions and the actuated positions are attained in same direction (either clockwise or counterclockwise) sequentially. The primed positions primarily relate to a condition of the rotary actuation mechanism, when a dose is loaded, and meant to be triggered on actuation of the rotary actuation mechanism. Whereas, the actuated positions primarily relate to a condition of the rotary actuation mechanism, when the rotary actuation mechanism is actuated and the dose is triggered. In order to attain such positions, the mechanical components of the rotary actuation mechanism may engage and disengage with each other to provide actuations to the rotary actuation mechanism. Furthermore, the rotary actuation mechanism is operable to sequentially alternate between the primed positions and actuated positions, to successfully load and trigger the dose. For example, a predetermined amount of dose is loaded at a rotational configuration of the rotary actuation mechanism at the primed position. In such an instance, a further rotation to the rotary actuation mechanism may trigger the predetermined amount of dose. In various examples, the primed positions may include rotational shifts of 20 degrees, 30 degrees, 40 degrees, 90 degrees, 180 degrees, and so forth from the initial position of the rotary actuation mechanism. Moreover, the actuated positions are further rotational shifts from the primed positions. For example, the actuated positions may include rotational shifts of 40 degrees, 60 degrees, 80 degrees, 180 degrees, 360 degrees, and so forth from the initial position of the rotary actuation mechanism.

The rotary actuation mechanism comprises the follower component, which is releasable to dispense a dose as the rotary actuation mechanism moves from the primed position to the next actuated position, and able to be primed as the rotary actuation mechanism moves from the actuated position to the next primed position. The term "follower component" relates to a hollow cylindrical element, and/or a tubular structure, provided therein to reciprocate or translate linearly, when the rotary actuation mechanism rotates between the primed positions and the actuated positions. Furthermore, when the rotary actuation mechanism moves from the primed position to the next actuated position, the follower component is released, and the dose is triggered through the nozzle. Similarly, when the rotary actuation mechanism moves from the actuated position to the next primed position, the follower component is moved in a reverse direction, and the dose is loaded therein, that is to be released at the next actuated position. Additionally, the shifting of primed positions and actuated positions are sequential and alternate to each other, to provide a simultaneous translation of the follower component.

Optionally, the portable inhaler has a longitudinal axis, wherein the follower component is releasable in a dispensing longitudinal direction and able to be primed in a metering longitudinal direction, and rotary movement of the rotary actuation mechanism is about the longitudinal axis. It is to be understood that the longitudinal axis is an imaginary line passing through a center of the portable inhaler. Furthermore, the follower component is operable to translate along the longitudinal axis, to successfully load and dispense the dose. Therefore, the follower component reciprocates forwardly to release the dose in the dispensing longitudinal direction, towards the nozzle. Similarly, the follower component reciprocates backwardly to be primed in the metering longitudinal direction, away from the nozzle. The follower component is translated linearly on rotation of the rotary actuation mechanism. The rotary actuation mechanism is rotated about the longitudinal axis to sequentially alternate between the primed positions and the actuated positions, to successfully load and deliver the dose.

Optionally, movement of the follower component is fixed with respect to rotation rotary movement of the rotary actuation mechanism. Herein, the movement of the follower component is fixed in the portable inhaler. As the movement of the follower component is fixed with respect to rotation of the rotary actuation mechanism, the the follower component is operable to reciprocate linearly along the longitudinal axis.

The rotary actuation mechanism comprises the rotary loading device, the rotary loading device comprising a cam component and a cage component wherein the cam component is caged by the cage component and engaged therewith by mutually interfering mechanical features such as to allow a predetermined limited rotational relative movement between the cage component and the cam component, the cam component having a radial cam; the radial cam having a first cam tooth surface on a leading edge of the tooth and a second cam tooth surface on a trailing edge of the tooth. Herein, the cage component is an upper spring cage component. The terms "cam component" and "cage component" used herein relates to cylindrical cams. It will be appreciated that cylindrical cams are mechanical elements that mimics a shape of a hollow cylinder having a thickness at cross sections. The cams also include crests followed by recesses, both alternatively around the circumference and throughout the curved surface. Furthermore, the cylindrical cams include mechanical features such as grooves, tooth, elevated threads at curved surfaces (internal and/or external). Notably, an engagement of the mechanical features allows a relative rotational movement between the cam component and the cage component. The predetermined limited rotational relative movement between the cage component and the cam component, refers to an angle gap between the relative movement of the cage and cam components. For example, the angle gap may be 2 degrees, 5 degrees, 10 degrees, and so forth. In such an instance, for each rotation (such as 180 degrees) of the cage component, the cam component may lag by the 2 degrees, 5 degrees, 10 degrees, respectively, as the angle gap provided therebetween. For example, when the predetermined limited rotational relative movement between the cage component and the cam component has the gap 10 degrees, then the cam component rotates to 170 degrees for 180 degrees rotation of the cage component.

Furthermore, the cam component has a radial cam to engage with the cage component to provide relative rotation therebetween. The "radial cam" used herein relates to elevated surfaces protruding from the curved surface of the cam component. The radial cam has the first cam tooth surface on the leading edge of the tooth and the second cam tooth surface on the trailing edge of the tooth, to successfully engage and disengage with the cage component. Furthermore, the first cam tooth surface on the leading edge of the tooth may refer to a narrower thickness at the beginning, meant to initiate the engagement of the cage component and the cam component; whereas, the second cam tooth surface on the trailing edge of the tooth may refer to broader thickness at the end, gradually increasing from beginning to the end, provided therein to hold the engagement of the cage component and the cam component.

Optionally, the predetermined limited relative rotational movement is in the range 2 to 30 degrees. In one example, the predetermined limited relative rotational movement is in the range 5 to 15 degrees. As mentioned herein above, the gap provided for the relative rotation between the cage component and the cam component, may vary from 2 degrees up to 30 degrees. It will be appreciated that at with each rotation there is a phase difference between rotations of the cage component and the cam component due to the predetermined limited relative rotational movement.

Optionally, the rotary movement of the rotary loading device between successive actuated positions of the rotary actuation mechanism is 180 degrees. In an instance, the primed position may be at a rotational shift of 180 degrees from the initial position of the rotary actuation mechanism, and the actuated position may be at a rotational shift of 360 degrees from the initial position of the rotary actuation mechanism. Therefore, each of the primed position and the actuated position are at an alternate of 180 degrees of rotation.

Optionally, the cage component has an inward facing recess into which an outward facing projection of the cam component fits loosely to provide the mutually interfering mechanical features. The inward facing recess relates to a root area of the radial cam that allows an engagement of crest of the interfering or engaging external tooth, such as the outward facing projection of the cam component. The "facing projection" used herein relates to a raised element of the cam component that engages and rests in the longitudinal direction and towards the nozzle of the portable inhaler. Furthermore, the engagement of the mutually interfering mechanical features are provided with a tolerance gap to loosely fit the inward facing recess into the outward facing projection of the cam component. Beneficially the tolerance gap may reduce wear and tear of the cam component, and allows ease of actuation.

Optionally, the rotary loading device and the follower component have a mutual helical camming arrangement, such that at least one of the rotary loading device and the follower component has a helical cam configured to engage an opposed camming feature of the opposite component to effect translation of the follower component in a metering longitudinal direction by relative rotation of the rotary loading device and the follower component. Furthermore, a reciprocation of the follower component is achieved by having a mutual helical camming arrangement between the rotary loading device and the follower component. Moreover, the presence of mutual helical camming arrangement and the relative rotary motion between the rotary loading device and the follower component, provides the linear translation of the follower component. It will be appreciated that the "helical camming" refers to arrangement of tooth at the curved surface in a form of helix. Furthermore, the mutual helical camming arrangement of the rotary loading device and the follower component, allows a transfer of rotational movement to the linear translation. Moreover, the follower component includes the opposed camming feature to restrict the follower component from translating in the metering longitudinal direction towards the nozzle, when engaged to the rotary loading device.

Optionally, the cam component and the follower component have the mutual helical camming arrangement. Furthermore, the engagement of the cam component and the follower is achieved by providing mutual helical camming arrangement therein, to successfully transform the rotary motion into linear translation or reciprocation. Beneficially, the cam component and the follower component having the mutual helical camming arrangement result in efficient transfer of power, as provided by the rotation of the rotary loading device.

Optionally, the cam component has the helical cam. The mutual helical camming arrangement of the cam component and the follower component is obtained by arranging the helical cam on the curved surface of the cam component. Moreover, the cam component includes the helical camming arrangement on both the curved surfaces (i.e. internal and external). The internal helical camming arrangement engages with the follower component, and the external helical camming arrangement engages with the cage component.

Optionally, the opposed camming feature is a zero-pitch ledge extending radially from the follower component. The term "zero-pitch ledge" relates to an outermost face of the camming feature having a flat edge with respect to slant edge of the camming feature. In order to block the linear movement of the follower component towards the nozzle, the opposed camming feature provides a flat surface, that is the zero-pitch ledge, extending radially from the follower component, and engages with the trailing edge of the cam component.

Optionally, the cam component has a zero-pitch extension to the helical cam and the follower component has a zero-pitch opposed camming feature to block movement of the follower in a dispensing longitudinal direction, and an edge to the zero-pitch extension beyond which movement of the follower component in its dispensing longitudinal direction is allowed. The cam component includes the zero-pitch extension to the helical cam and the follower component has the zero-pitch opposed camming feature, to restrict the movement of the follower in the dispensing longitudinal direction. In such an instance, the zero-pitch extension of the cam component and the zero-pitch opposed camming feature of the follower component mutually aligns at the radial circumference to block the movement of the follower in the dispensing longitudinal direction. Additionally, the arrangement of the zero-pitch extension of the cam component and the zero-pitch opposed camming feature of the follower component is such that a slight shift in the arrangement allows the follower component to move in the dispensing longitudinal direction. In such an instance, the zero-pitch opposed camming feature of the follower component disengages with the zero-pitch extension of the cam component to allow a passage of the mutual camming features thereof, and allowing the follower component to move in the dispensing longitudinal direction.

Optionally, the follower component is biased in the dispensing longitudinal direction by a spring. That is, movement to the follower component is provided by the spring to translate along the longitudinal axis. In an example, the spring may be provided at a base of the follower component, and thereby the movement of the follower component is upwards. In another example, the spring may be provided at an opening of the container (containing the fluid). Particularly, such containers include a spring mechanism along with a capillary tube tensioning the spring. Therefore, an arrangement of the spring may force the actuation of the follower component.

The rotary actuation mechanism comprises the button, which is translatable between a central position and an extended position, comprising a diversionary tooth having a first tooth surface engageable by the first cam tooth surface of a radial cam of the cam component upon rotary movement of the rotary actuation mechanism to its primed position to translate the button to its extended position, the diversionary tooth having a second tooth surface which can engage the second cam tooth surface of the radial cam to effect rotary movement of the rotary actuation mechanism to its actuated position as the button translates to its central position thereby releasing the follower component. The term "button" herein relates to a mechanical switch which, when in operation, provides a control on the rotational movement of the cam component. The button is arranged in a recess at the circumference of the cage component. The "central position", stated herein, relates to a condition when the button has been pressed to actuate the inhaler, whereas the extended position relates to a condition when the button is shifted radially outward from the circumference of the cage component in the primed state of the device. In an instance when the button is at the rest position, the diversionary tooth having the first tooth surface circumferentially engage to the first cam tooth surface of the radial cam of the cam component upon rotary movement of the rotary actuation mechanism to its primed position, in order to translate the button to its extended position. In an instance, when the rotary actuation mechanism is rotated to 180 degrees from its rest position (with the cam component being rotated to 170 degrees) and the follower component moves to downward position, then the radial cam of the cam component translates the button to its extended position. Furthermore, when an external force is applied to the button, the diversionary tooth having a second tooth surface engages with the second cam tooth surface of the radial cam to effect rotary movement of the rotary actuation mechanism to its actuated position, thereby releasing the follower component about the longitudinal axis. For an instance, the external force may be a thumb press, or a finger press by a user. Furthermore, while actuation, the diversionary tooth travels through second cam tooth surface of the radial cam, thereby shifting the cam component from 170 degrees to 180 degrees. Moreover, upon actuation, the diversionary tooth travels through second cam tooth surface of the radial cam, and allows disengagement of the zero-pitch extension of the cam component and the zero-pitch opposed camming feature, thereby releasing the follower component.

Optionally, the button is translatable transversely to the longitudinal axis. Furthermore, the central position and the extended position of the button translates radially inwards and radially outwards to the longitudinal axis.

Moreover, it may be understood that priming of the rotary actuation mechanism drives the button radially towards the longitudinal axis, whereas actuating the radial cam drives the button radially away from the longitudinal axis.

Optionally, the cage component has an upward facing recess into which the diversionary tooth of the button fits loosely to allow the diversionary tooth to move into the upward facing recess, while the recess rotates about the longitudinal axis. Furthermore, the upward facing recess accommodates the movement of the diversionary tooth into the upward facing recess, while translation of the button from central position to the extended position. Herein, the upward facing recess rotates along with the cage component about the longitudinal axis.

Optionally, the rotary actuation mechanism is moved from its actuated position to its primed position by applying a torque to the cage component. Furthermore, the rotary actuation mechanism is moved from its actuated position to its primed position by twisting the cage component. In an instance, twisting of the cage component is performed by a user.

Optionally, the portable inhaler is a low volatility liquid atomizer. Furthermore, the disclosed portable inhaler includes a container containing low volatile liquid. For example, the liquid may be Fluticasone and salmeterol (Advair Diskus), Mometasone and formoterol (Dulera), and the like.

Optionally, the energy of atomization is provided by a stored mechanical force. Herein, the stored mechanical force may be provided by an actuated spring, an electrically charged actuator, or any other suitable means without any limitations.

DETAILED DESCRIPTION OF THE DRAWINGS

Figure 1B:
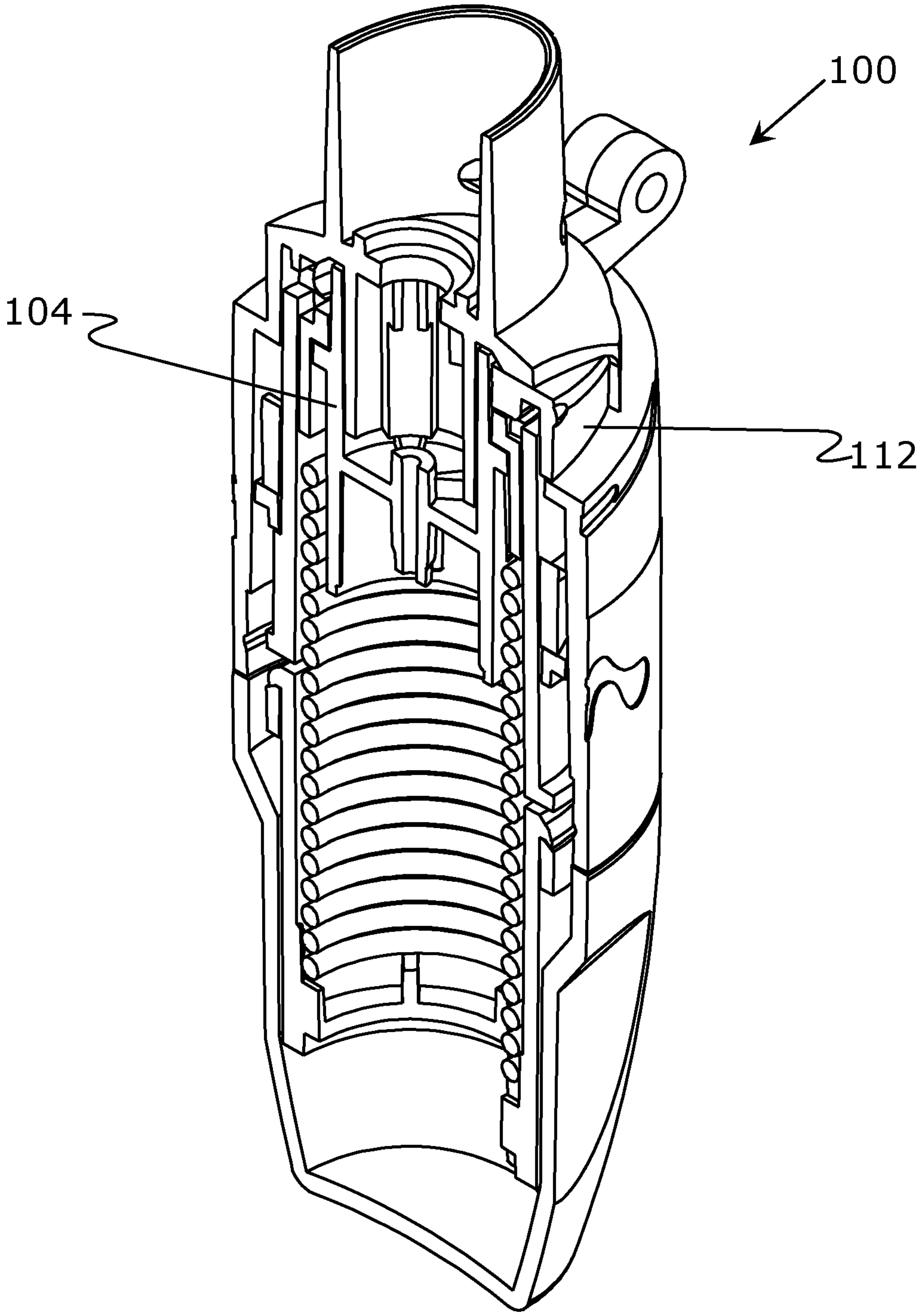
FIG. 1B is a perspective view of a portable inhaler, in accordance with an embodiment of the present disclosure, sectioned vertically to reveal a cross section of the rotary actuation mechanism.

Referring to FIG. 1, illustrated is a perspective view of a portable inhaler 100, in accordance with an embodiment of the present disclosure. The detail of FIG. 1 is expanded in FIG. 5A, which should also be referred to in relation to the ensuing paragraph. The portable inhaler 100, has a rotary actuation mechanism 102 moveable sequentially and alternately between primed positions and actuated positions. The rotary actuation mechanism 102 comprises a follower component 104, which is releasable to dispense a dose (not shown) as the rotary actuation mechanism 102 moves from the primed position to the next actuated position, and able to be primed as the rotary actuation mechanism 102 moves from the actuated position to the next primed position. The rotary actuation mechanism 102 comprises a rotary loading device 106. The rotary loading device 106 comprises a cam component 108 and a cage component 110, such that the cam component 108 is caged (enclosed) by the cage component 110 and engaged therewith by mutually interfering mechanical features such as to allow a predetermined limited rotational relative movement between the cage component 110 and the cam component 108. For example, a tongue 113 of the cam component 108 protrudes into a gap 111 (see FIG. 5C) in the inner wall of the cage component 110, such that the tongue has some free movement in the gap. The rotary actuation mechanism 102 comprises a button 112, which is translatable between a central position and an extended position. The button 112 comprises a diversionary tooth 114 having a first tooth surface 116 engageable by the first cam tooth surface 118 of a radial cam 120 of the cam component 108 upon rotary movement of the rotary actuation mechanism 102 to its primed position, to translate the button 112 to its extended position. Since this embodiment involves a 180-degree rotation of the rotary loading device 106 between actuations, the cam component 108 has two radial cams 120. The diversionary tooth 114 has a second tooth surface 122 (see FIG. 3) which can engage the second cam tooth surface 124 (see FIG. 2A) of the radial cam 120 to effect rotary movement of the rotary actuation mechanism 102 to its actuated position, as the button 112 translates to its central position, thereby releasing the follower component 104.

Figure 2A:
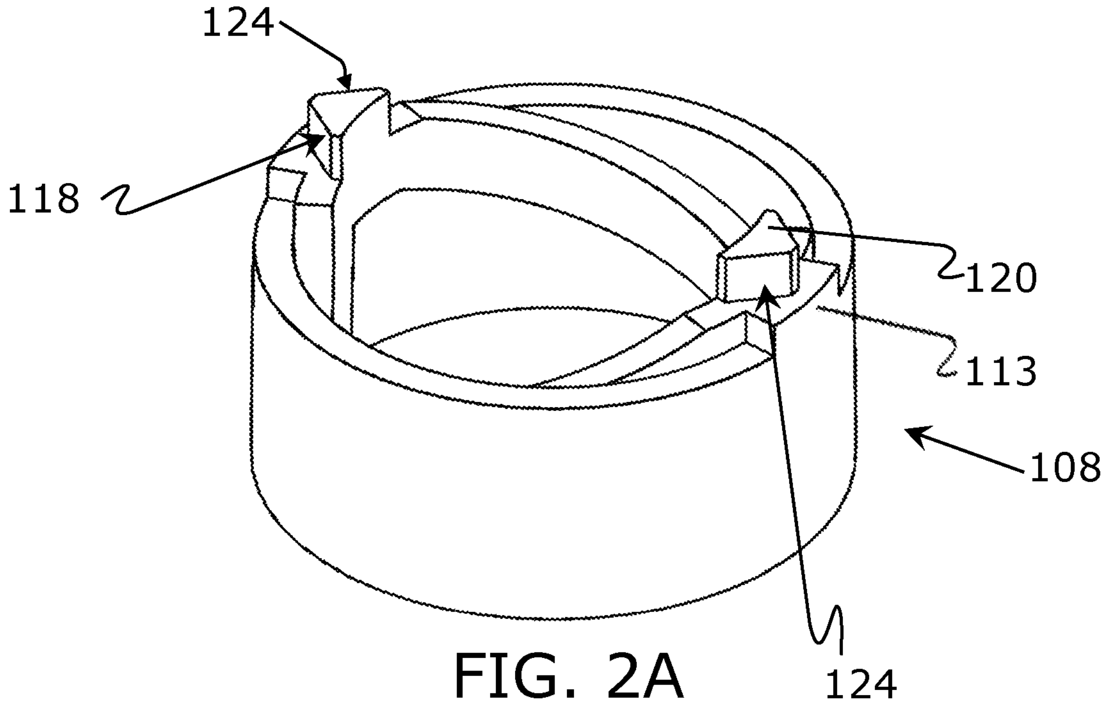
FIG. 2A is a perspective view of the cam component seen from a point to one side above the cam component.
Figure 2B:
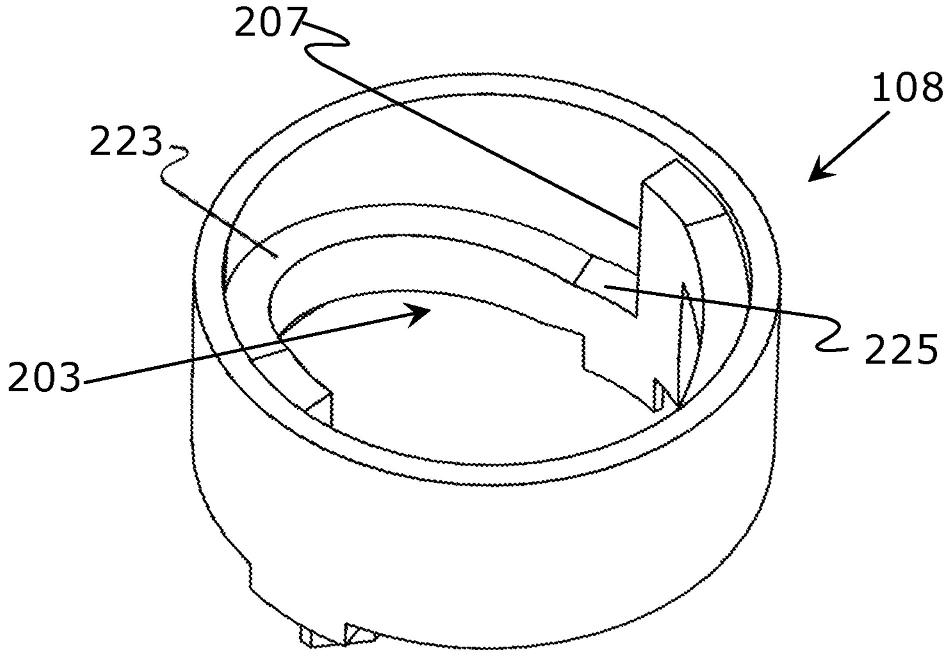
FIG. 2B is a perspective view of the cam component seen from a point to one side below the cam component.

The cam component shown in FIGS. 2A and 2B is an open structure, having generally cylindrical shape with diametrically positioned cam teeth 120 extending from the top of the cylinder. Each cam tooth 120 has a first cam tooth surface 118 and a second cam tooth surface 124. There is an inward cam 203 comprising a pair of helical cams 223 extending from the inside surface of the cylinder and these cams each extend downwards just short of half way round the cylinder, followed by a horizontal portion 225, then an upward first cliff edge 207. Each first cliff edge 207 is in a predetermined rotational position relative to the rotational position of each cam tooth.

Figure 3:
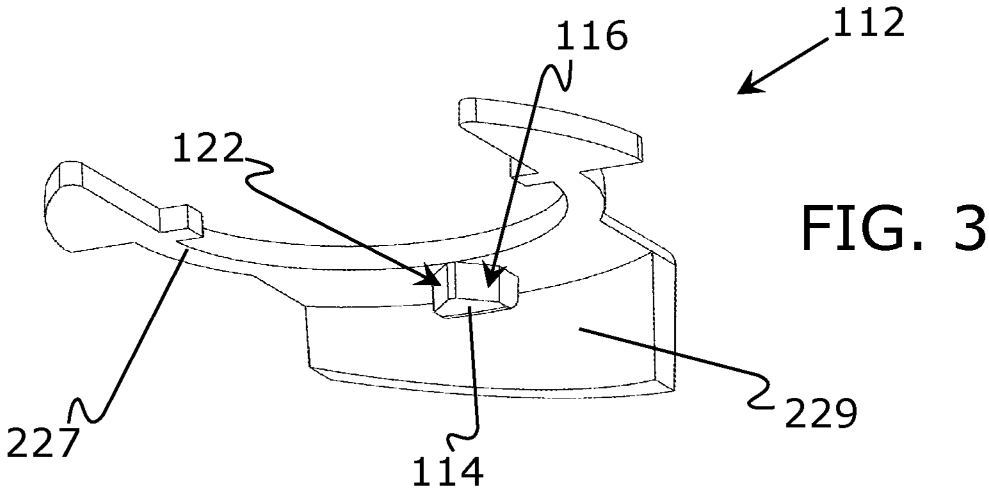
FIG. 3 is a perspective view of the button seen from a point to one side below the button.

The button 112 shown in FIG. 3 has a yoke 227 to key into other components of the portable inhaler to provide limited radial movement. It has a sloped external face 229 which aligns with a slope on the outside profile of the portable inhaler. It has a diversionary tooth 114 with a pointed end aligned with the sloped external face, such that external pressure applied to the sloped external face directs the diversionary tooth in the direction of the pointed end.

Figure 4:
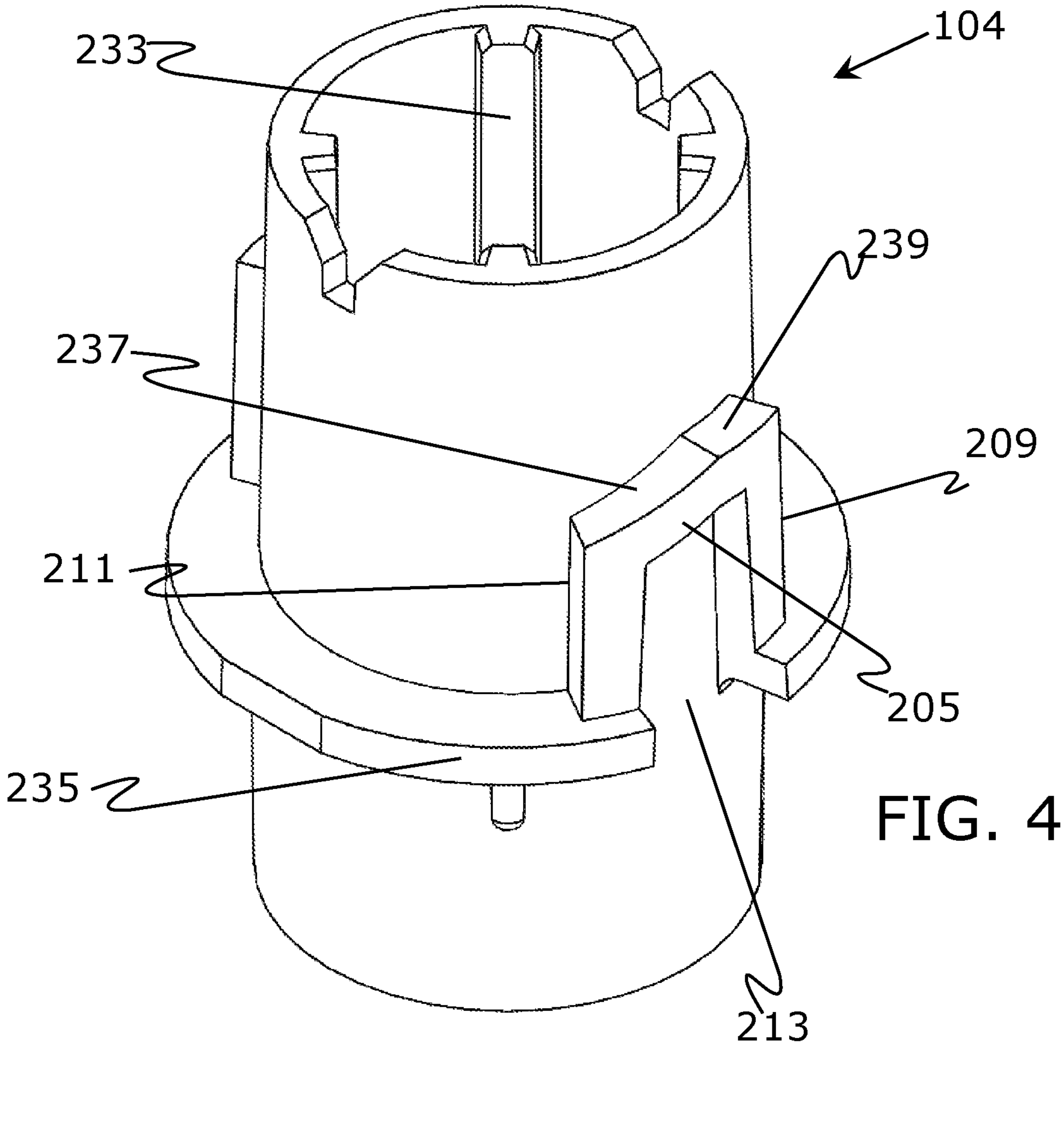
FIG. 4 is a perspective view of the follower component seen from a point to one side above the follower.

The follower 104 shown in FIG. 4 is an open structure, having generally cylindrical shape with vertical ribs 233 extending from the internal surface to allow vertical movement in the portable inhaler, but no rotational movement. The vertical ribs 233 engage snugly into grooves in a chassis of the inhaler (not shown), such that rotational movement relative to the portable inhaler, including the mouthpiece, is prevented. The follower 104 has a circumferential ledge 235 on the external surface. There is a pair of breaks 213 in the circumferential ledge 235; the breaks 213 are optional, but allow more economic manufacture. Each break is bridged by an outward cam 205. The outward cam has a second cliff edge 209, a third cliff edge 211, a short helical portion 237 leading into a short horizontal portion 239. The second cliff edge 209 is adjacent the horizontal portion and the third cliff edge 211 is adjacent the helical portion 237. It will be appreciated that the dimensions of the outward cam 205 are designed to operate with features of the inward cam 203 of the cam component 108, so the positioning of the vertical ribs 233 and grooves provides a datum for the relative positioning of the outward 205 cam and inward cam 203.

Referring to FIGS. 5A-5H, illustrated are perspective views of various stages of dispensing a dose using the portable inhaler 100, in accordance with an embodiment of the present disclosure. It may be understood by a person skilled in the art that the various stages of dispensing a dose using the portable inhaler 100, as depicted, are for sake of clarity only and should not be construed to unduly limit the scope of the claims herein. The person skilled in the art will recognize many variations, alternatives, and modifications of embodiments of the present disclosure.

Figure 5A:
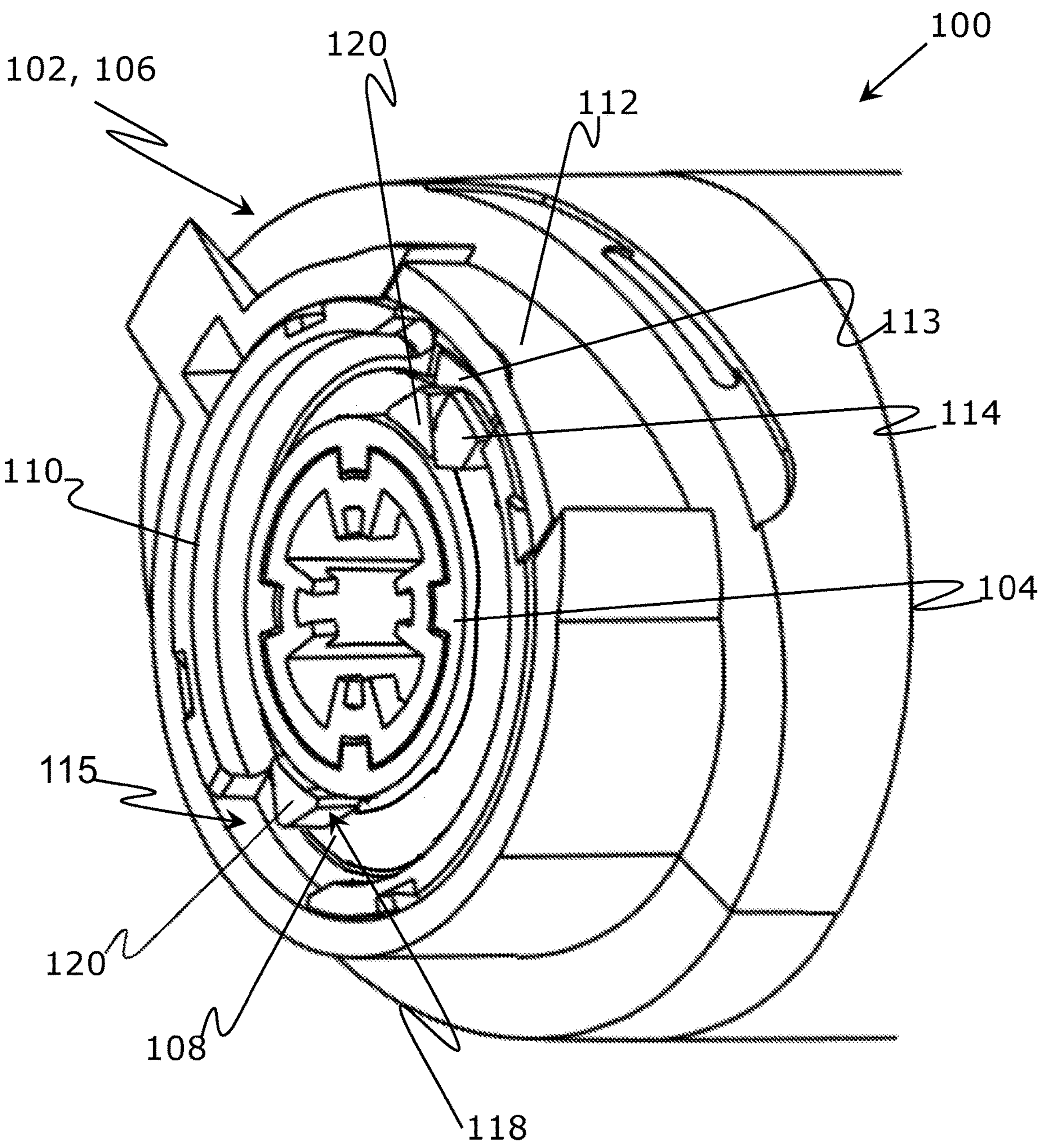
FIG. 5A is an expanded view of the portable inhaler shown in FIG. 1A, which is in its rest position.
Figure 5B:
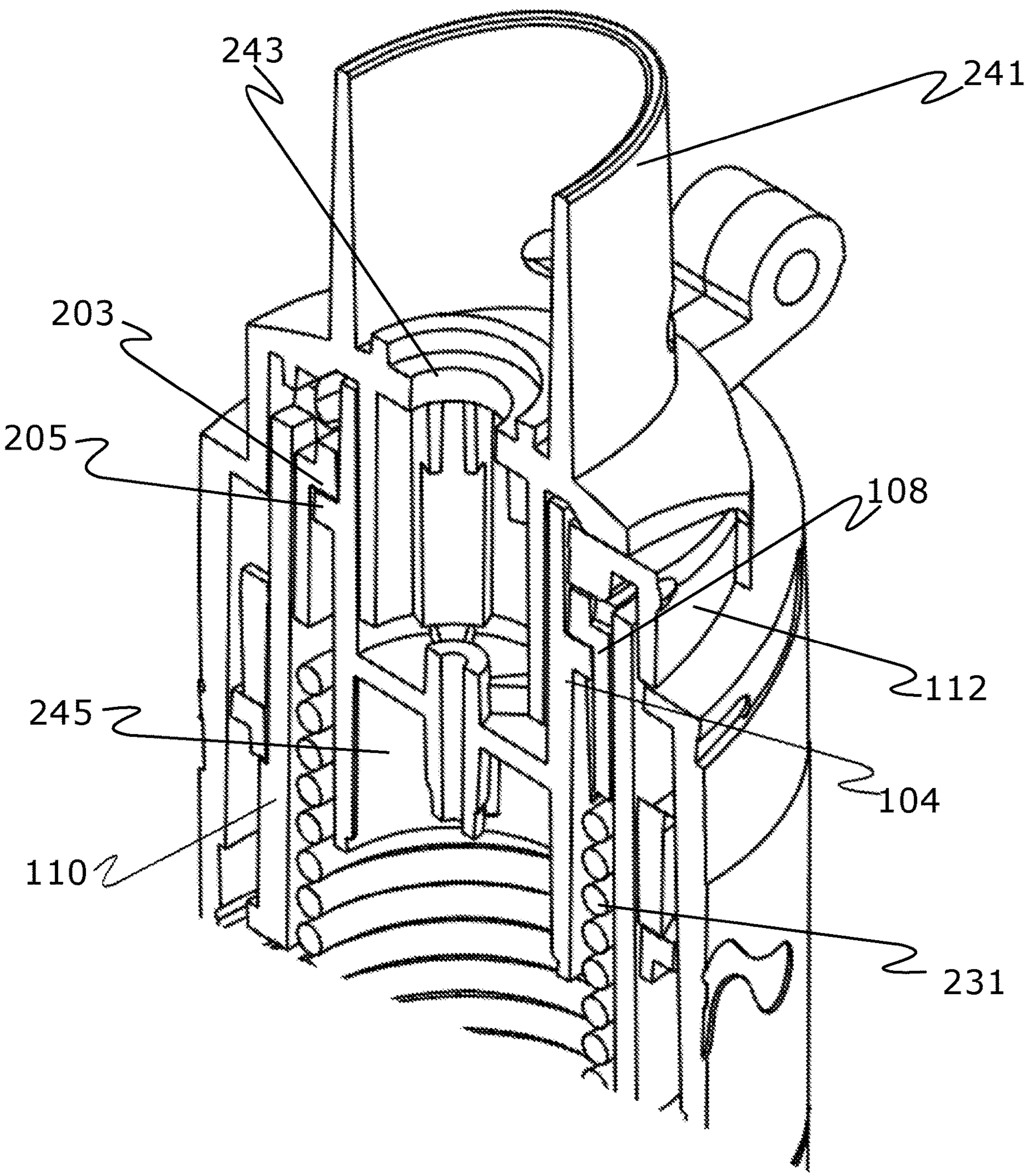
FIG. 5B is an expanded view of the portable inhaler shown in FIG. 1B, which is in its rest position.

In FIGS. 5A and 5B, there are shown sectioned views of of the portable inhaler 100, when in a rest position, which corresponds to the initial position described earlier. As shown in FIG. 5A and 5B, the button 110 is in depressed position and the follower component 104 is at highest position. FIG. 5B shows the follower component 104, cam component 108, cage component 110 and spring 231. It also shows inward cam 203 of the cam component engaging an outward cam 205 of the follower. Furthermore, the mouthpiece 241 and nozzle 243 of the portable inhaler are shown, and a lower part of the follower in the form of a follower housing 245 which is configured to grip a container of drug solution (not shown) to be dispensed.

Figure 5C:
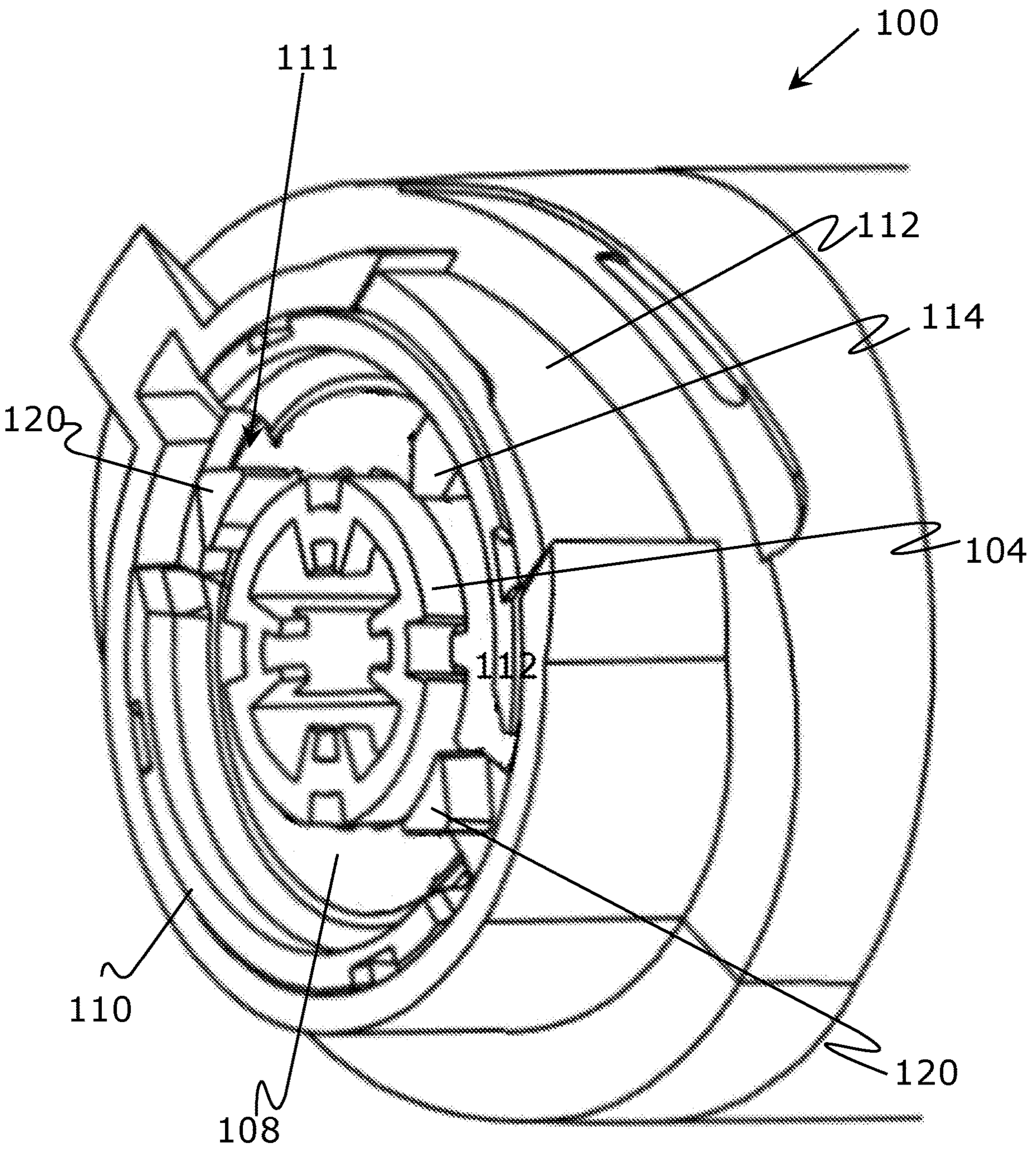
FIG. 5C is an expanded view of the portable inhaler sectioned horizontally, in a loading position.
Figure 5D:
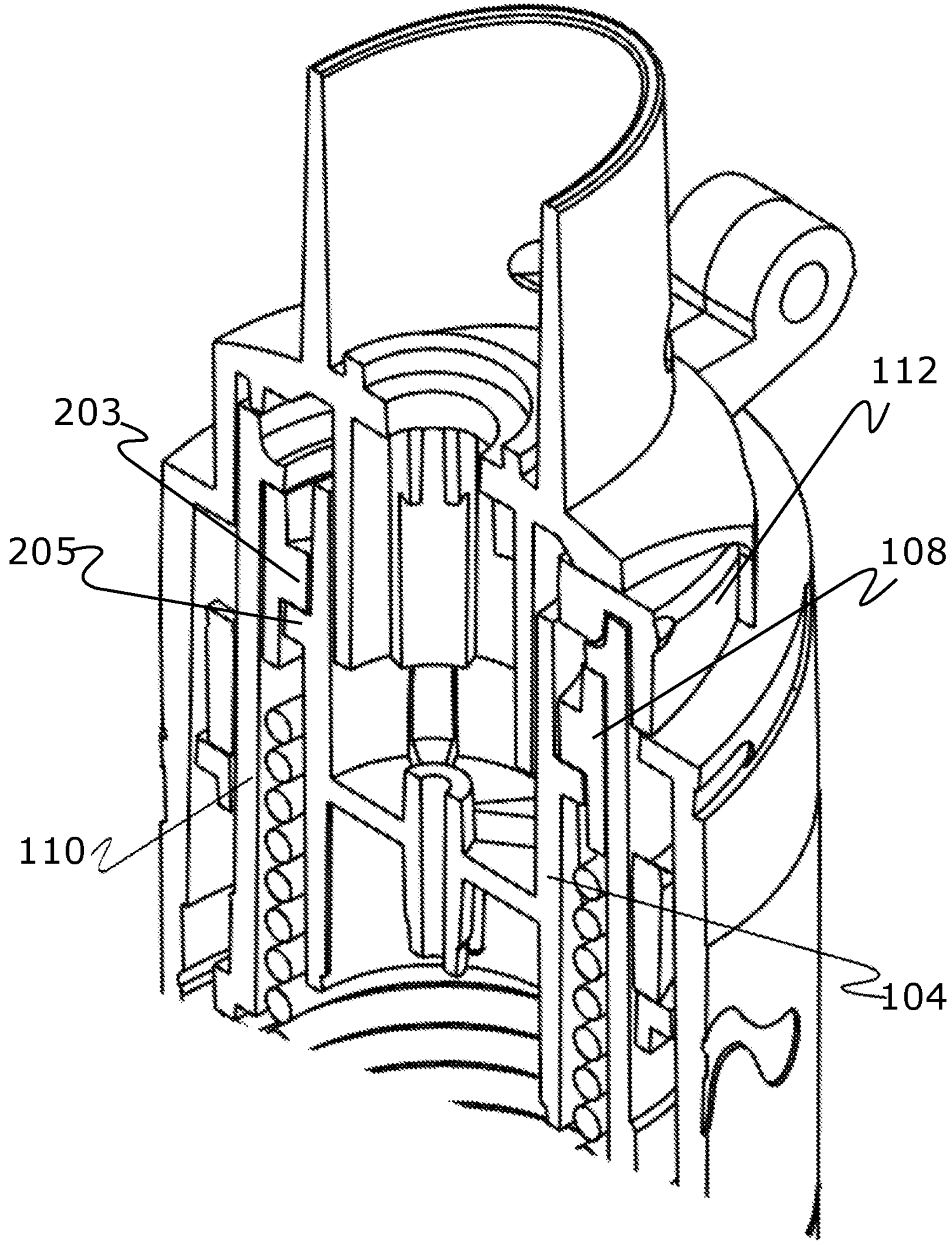
FIG. 5D is an expanded view of the portable inhaler, sectioned vertically, in a loading position.

In FIGS. 5C and 5D, there is shown an intermediate stage when loading of dose (not shown) is performed. To get to this stage, the cage component 110 is rotated from the rest position to an intermediate position, during which after 10 degrees of rotation it starts to drive the cam component. In FIG. 5C, the cam component 108 is shown at an angle of 90 degrees from the rest position. Furthermore, the follower component 104 has moved to a downward position (i.e. intermediate position) from the highest position, as shown in FIG. 5D, by the action of the inward cam 203 of the cam component engaging the outward cam 205 of the follower.

Figure 5E:
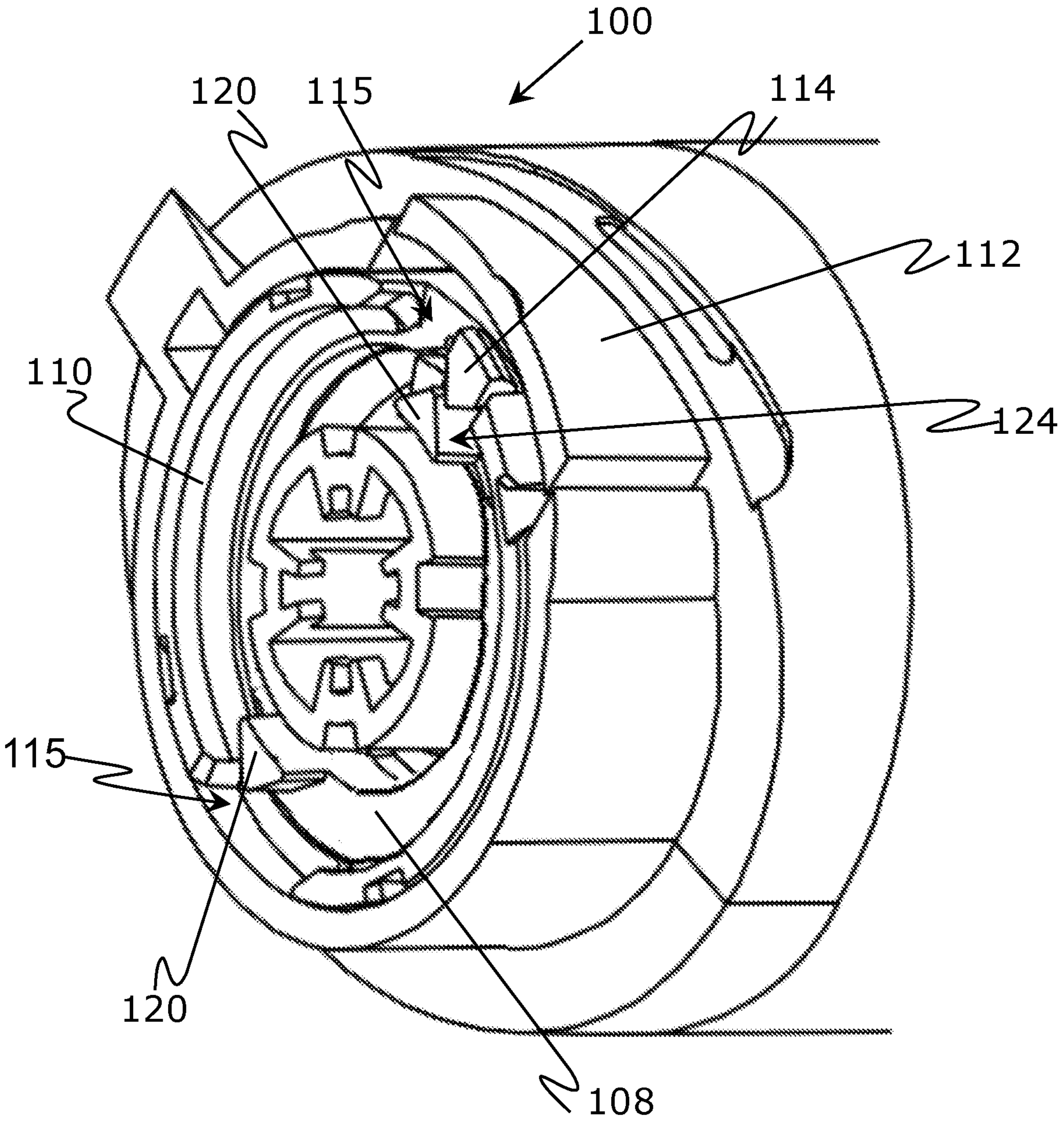
FIG. 5E is an expanded view of the portable inhaler sectioned horizontally, in a primed position.
Figure 5F:
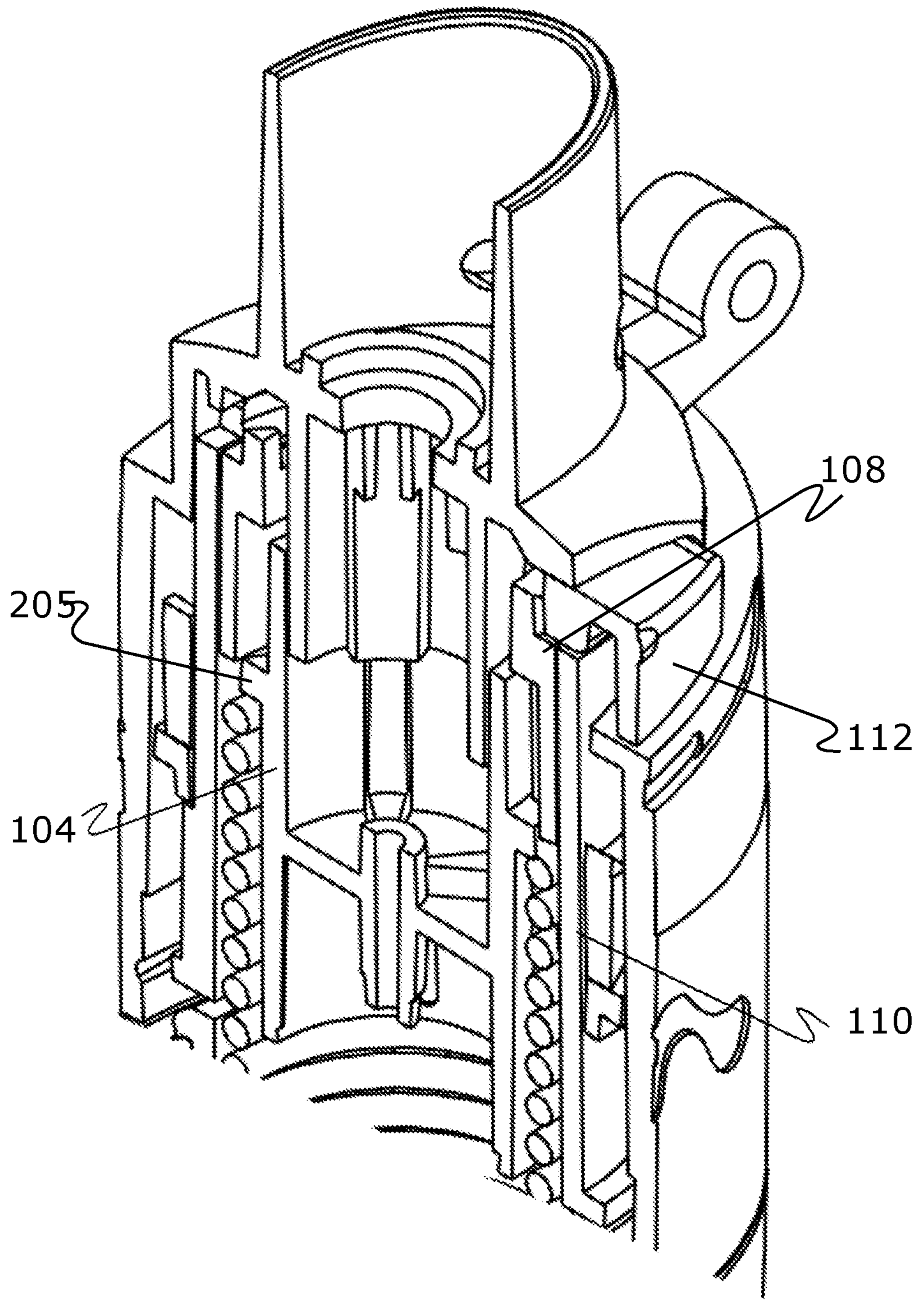
FIG. 5F is an expanded view of the portable inhaler, sectioned vertically, in a primed position.

In FIGS. 5E and 5F, there is shown a stage when the dose (not shown) is loaded, i.e. the inhaler is primed. In this stage, the cage component 110 has rotated from the intermediate stage to an angle 180 degrees (i.e. to a primed position) from the rest position. However, the cam component 108 has rotated only 170 degrees from the rest position due to a predetermined limited rotational relative movement which is of 10 degrees, provided between the cage component 110 and the cam component 108. The cage component has an outer raised circumferential wall. The circumferential wall has two breaks 115 in it each over a narrow angle range. In most positions of the cage component 110, the wall prevents outward movement of the button, in particular movement of the diversionary tooth 114 of the button 112. As the cage component approaches the loaded position and until it passes the dispensed position, the break in the wall allows the button to move outwardly. Furthermore, the follower component 104 moves to a further downward position from the intermediate downward position (as depicted in FIGS. 5E and 5F). Herein, the radial cam tooth 120 of the cam component 108 pushes the diversionary tooth 114 of the button 110 radially outwards, when the first cam tooth surface of the radial cam tooth engages the first tooth surface of the diversionary tooth of the button. Here the respective angles of the teeth allow the tangential force to be resolved in a radial direction.

Figure 5G:
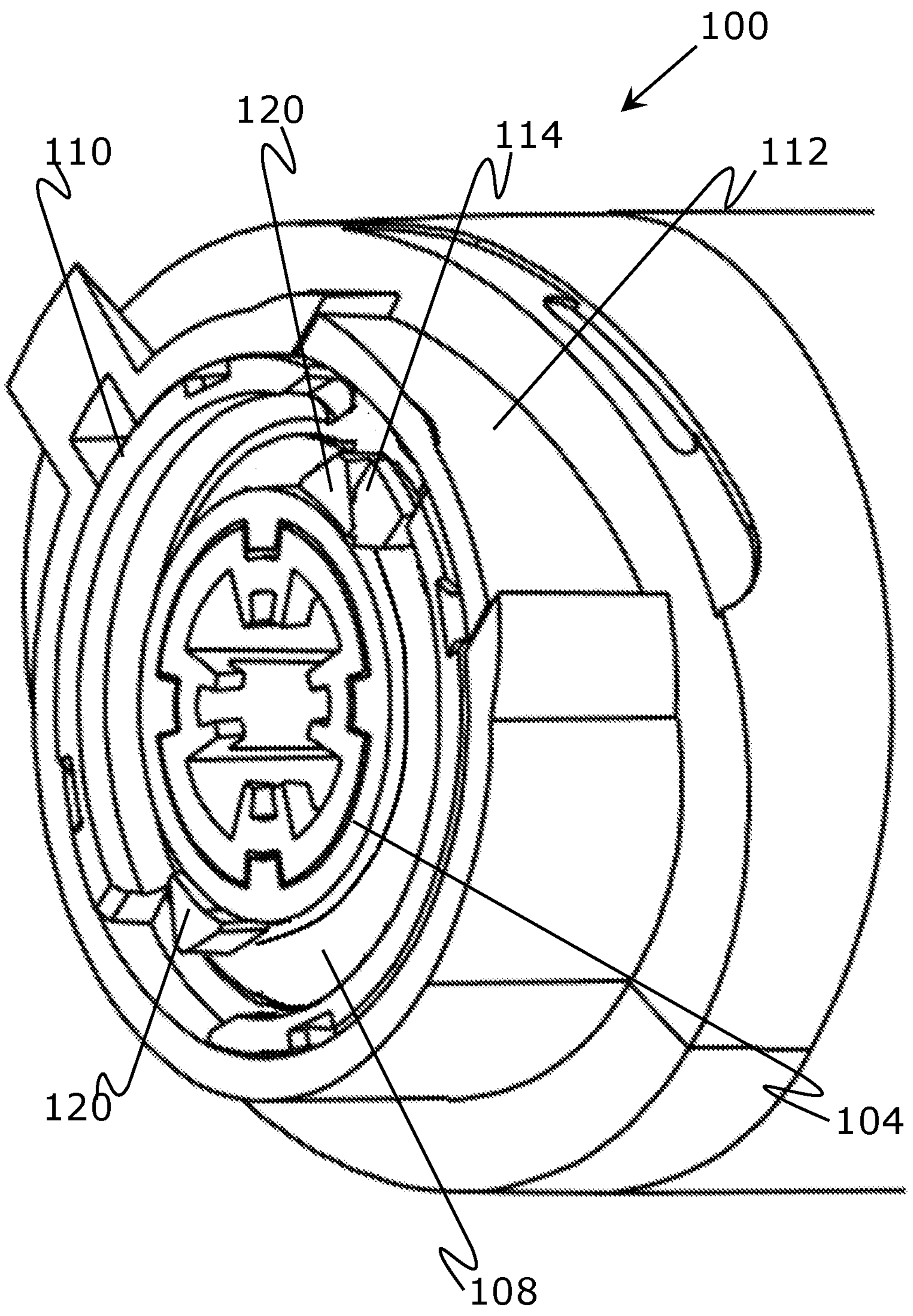
FIG. 5G is an expanded view of the portable inhaler sectioned horizontally, in a dispensed position.
Figure 5H:
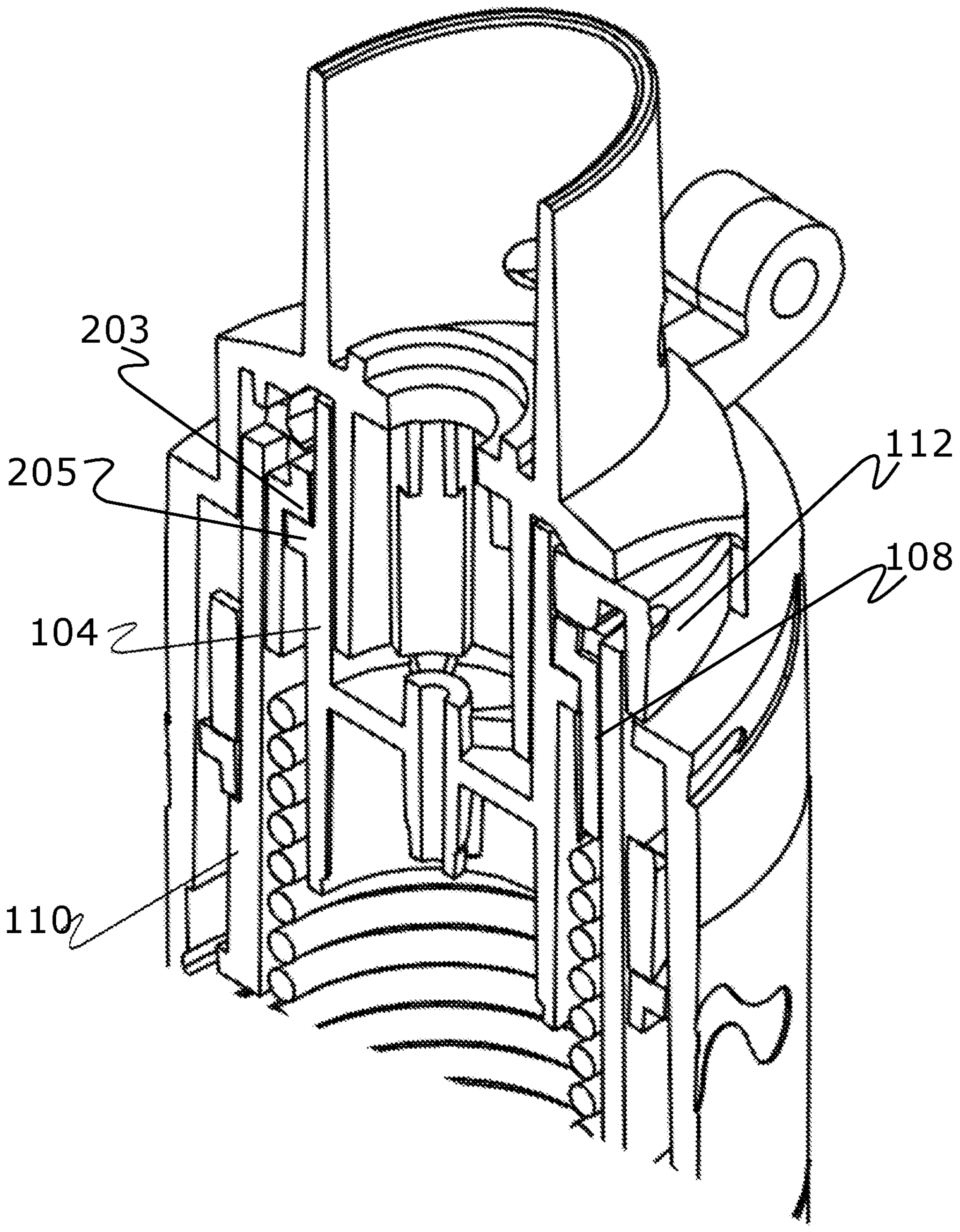
FIG. 5H is an expanded view of the portable inhaler, sectioned vertically, in a dispensed position.

In FIGS. 5G and 5H, there is shown a stage when the dose (not shown) is dispensed, i.e. the inhaler is actuated. From the loaded stage, the button 112 is pressed and the second tooth surface of the diversionary tooth 114 engages the second cam tooth surface 124 of the radial cam 120 of the cam component 108. This causes the cam component 108 (same as in the rest position) completing 180 degrees of rotation from the rest position. During this rotation (see FIGS. 2A, 2B and 4), a first cliff edge 207 of the inward cam 203 of the cam component comes into alignment with a second cliff edge 209 of the outward cam 205 of the follower. Consequently, the follower component 104 shoots to the highest position under the released force of spring 231, and the rotary loading device 106 moves to an actuated position (same as the rest position), and the dose (not shown) is dispensed.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A portable inhaler, comprising:

a rotary actuation mechanism moveable sequentially and alternately between primed positions and actuated positions;

wherein the rotary actuation mechanism comprises:

a follower component, the follower component being releasable to dispense a dose as the rotary actuation mechanism moves from a primed position of the primed positions to an actuated position of the actuated positions, and able to be primed as the rotary actuation mechanism moves from the actuated position to a second primed position of the primed positions;

a rotary loading device, the rotary loading device comprising a cam component and a cage component, wherein the cam component is caged by the cage component and engaged therewith by mutually interfering mechanical features to allow a predetermined limited rotational relative movement between the cage component and the cam component;

a button, the button being translatable between a central position and an extended position, the button configured to be engaged by the cam component upon rotary movement of the rotary actuation mechanism to the primed position to translate the button to the extended position, and the button configured to engage the cam component to effect rotary movement of the rotary actuation mechanism to the actuated position as the button translates to the central position thereby releasing the follower component.

2. The portable inhaler as in claim 1, wherein the cam component comprises a cam tooth, the cam tooth being a radial tooth, the radial tooth comprising a first cam tooth surface on a leading edge of the radial tooth and a second cam tooth surface on a trailing edge of the radial tooth;

the button comprising a diversionary tooth comprising a first tooth surface engageable by the first cam tooth surface of the radial tooth of the cam component upon rotary movement of the rotary actuation mechanism to its-the primed position to translate the button to the extended position, the diversionary tooth comprising a second tooth surface configured to engage the second cam tooth surface of the radial tooth to effect rotary movement of the rotary actuation mechanism to its-the actuated position as the button translates to its the central position thereby releasing the follower component.

3. The portable inhaler as in claim 1, comprising a longitudinal axis, wherein the follower component is releasable in a dispensing longitudinal direction and able to be primed in a metering longitudinal direction, and rotary movement of the rotary actuation mechanism is about the longitudinal axis.

4. The portable inhaler as in claim 3, wherein movement of the follower component is fixed with respect to rotary movement of the rotary actuation mechanism.

5. The portable inhaler as in claim 3, wherein the button is translatable transverse to the longitudinal axis.

6. The portable inhaler as in claim 1, wherein the predetermined limited relative rotational movement is in the range 2 to 30 degrees.

7. The portable inhaler as in claim 6, wherein the predetermined limited relative rotational movement is in the range 5 to 15 degrees.

8. The portable inhaler as in claim 1, wherein the rotary movement of the rotary loading device between successive actuated positions of the actuated positions of the rotary actuation mechanism is 180 degrees.

9. The portable inhaler as in claim 1, wherein the cage component comprises an inward facing recess into which an outward facing projection of the cam component fits loosely to provide the mutually interfering mechanical features.

10. The portable inhaler as in claim 1, wherein the cage component comprises an upward facing recess into which a diversionary tooth of the button fits loosely to allow the diversionary tooth to move into the upward facing recess, while the recess rotates about a longitudinal axis.

11. The portable inhaler as in claim 1, wherein the rotary loading device and the follower component have a mutual helical camming arrangement, such that at the rotary loading device and/or the follower component comprises a helical cam of the mutual helical camming arrangement configured to engage an opposed camming feature of the mutual helical camming arrangement of an opposite component to effect translation of the follower component in a metering longitudinal direction by relative rotation of the rotary loading device and the follower component.

12. The portable inhaler as in claim 11, wherein the cam component and the follower component comprise the mutual helical camming arrangement.

13. The portable inhaler as in claim 12, wherein the cam component comprises the helical cam.

14. The portable inhaler as in claim 13, wherein the cam component comprises a zero-pitch extension to the helical cam and the follower component comprises the opposed camming feature in a form of a zero-pitch opposed camming feature to block movement of the follower component in a dispensing longitudinal direction, and the cam component comprises an edge to the zero-pitch extension beyond which movement of the follower component in the dispensing longitudinal direction is allowed.

15. The portable inhaler as in claim 11, wherein the opposed camming feature is a zero-pitch ledge extending radially from the follower component.

16. The portable inhaler as in claim 1, wherein the follower component is biased in a dispensing longitudinal direction by a spring.

17. The portable inhaler as in claim 1, wherein the rotary actuation mechanism is moved from the actuated position to the primed position by applying a torque to the cage component.

18. The portable inhaler as in claim 1, wherein the portable inhaler is a low volatility liquid atomizer.

19. The portable inhaler as in claim 18, wherein an energy of atomization of the portable inhaler is provided by a stored mechanical force.

* * * * *